(12) United States Patent
Sherwin et al.

(10) Patent No.: US 10,839,290 B2
(45) Date of Patent: Nov. 17, 2020

(54) SYSTEM AND METHOD TO EVALUATE DECISION-MAKING

(71) Applicant: deCervo LLC, New York, NY (US)

(72) Inventors: Jason Sherwin, Brooklyn, NY (US); Jordan Muraskin, New York, NY (US)

(73) Assignee: deCervo LLC, New York, NY (US)

( * ) Notice: Subject to any disclaimer, the term of this patent is extended or adjusted under 35 U.S.C. 154(b) by 1065 days.

(21) Appl. No.: 15/297,630

(22) Filed: Oct. 19, 2016

(65) Prior Publication Data

US 2017/0109627 A1  Apr. 20, 2017

Related U.S. Application Data

(60) Provisional application No. 62/243,234, filed on Oct. 19, 2015.

(51) Int. Cl.
 *G06N 5/02* (2006.01)
 *G06N 3/08* (2006.01)
 *G16H 40/63* (2018.01)

(52) U.S. Cl.
 CPC ............ *G06N 3/08* (2013.01); *G06N 5/02* (2013.01); *G06N 5/022* (2013.01); *G16H 40/63* (2018.01)

(58) Field of Classification Search
 CPC  G06N 5/02; G06N 3/08; G06N 5/022; G16H 40/63
 USPC ........................................................ 706/46
 See application file for complete search history.

(56) References Cited

U.S. PATENT DOCUMENTS

| | | |
|---|---|---|
| 8,731,650 B2 | 5/2014 | Sajda |
| 2009/0024475 A1 | 1/2009 | Pradeep |
| 2012/0036004 A1 | 2/2012 | Pradeep |
| 2013/0034837 A1* | 2/2013 | Clapp ............... G09B 5/06 434/247 |
| 2013/0158883 A1 | 6/2013 | Hasegawa |
| 2015/0216439 A1 | 8/2015 | Muraskin |
| 2015/0246232 A1 | 9/2015 | Kameneva |
| 2015/0248470 A1 | 9/2015 | Coleman |

(Continued)

OTHER PUBLICATIONS

PCT, Notification of Transmittal of the International Search Report and the Written Opinion of the International Searching Authority, or the Declaration, in International Application No. PCT/US16/57698, dated Jan. 27, 2017 (18 pages).

(Continued)

*Primary Examiner* — Lut Wong
(74) *Attorney, Agent, or Firm* — McAndrews, Held & Malloy, Ltd.

(57) ABSTRACT

Systems and methods to analyze decision-making. A processor accesses at least one storage medium storing a high-fidelity recording, the high-fidelity recording includes a stimulus event and one or more rules associated with the stimulus event. The processor presents the high-fidelity recording through a presentation device. The processor receives neural metrics from a neural sensor while the high-fidelity recording is being presented. The processor applies rules to generate reference metrics associated with the stimulus event. The processor modifies elements of the high-fidelity recording based on the reference metrics to distinguish the stimulus event within the high fidelity recording. The processor presents the modified recording by the presentation device.

20 Claims, 7 Drawing Sheets

(56) References Cited

U.S. PATENT DOCUMENTS

2016/0143573 A1 5/2016 Brickman
2016/0242669 A1 8/2016 Muraskin

OTHER PUBLICATIONS

Muraskin, Jordan et al., Brain Dynamics of Post-Task Resting State are Influenced by Expertise: Insights From Baseball Players, Human Brain Mapping 00:00-00 (2016). (18 pages).
Sherwin, Jason and Gaston, Jeremy, Soldiers and marksmen under fire: monitoring performance with neural correlates of small arms tire localization, Frontiers in Human Neuroscience, Mar. 2013, vol. 7, Article 67. (14 pages).
Sherwin, Jason and Gaston, Jeremy, Experience Does Not Equal Expertise in Recognizing Infrequent Incoming Gunfire: Neural Markers for Experience and Task Expertise at Peak Behavioral Performance, PLOS One | DOI:10.1371/journal.pone.0115629, Feb. 6, 2015, (24 pages).

\* cited by examiner

SYSTEM AND METHOD TO EVALUATE DECISION-MAKING

CROSS REFERENCE TO RELATED APPLICATIONS

This application claims priority to U.S. Provisional Patent Application Ser. No. 62/243,234, filed Oct. 19, 2015, entitled "Evaluating a Subject's Decision-Making in Response to Video Stimulation". The entirety of U.S. Provisional Patent Application Ser. No. 62/243,234 is incorporated herein by reference.

BACKGROUND

Generally, this application relates to neuroimaging, processes, and recordings suitable for quantifying decision-making in response to stimuli. One example of this disclosure is for use with audio/visual presentations showing scenes containing stimuli and monitoring decisions made in response to those scenes.

One way for performing neuroimaging data analysis is to provide subjects with stimuli that have precisely controlled events to which a neuroimaging data stream is locked. However, in the case of "real-world" audio/visual recordings (as opposed to animations, and hereinafter referred to more simply as "video"), this has not been possible.

Another way of analyzing continuous neuroimaging data in response to a recording is to use a data analysis technique called reliable components analysis (RCA) or canonical components analysis (CCA). Neither of these techniques, though, take into account neural data leading up to or following an external event. Rather, they are focused on the locking between neuroimaging data of different sessions and/or subjects.

Previous attempts to solve the problem of video-based decision-making with time-precise neural and behavioral data have recreated these scenes with computerized graphics or otherwise precisely controlled electronically-produced events (e.g., as in animation or video game design). However, the fidelity of these simulations may not be high enough to adequately stimulate the nervous systems to evoke the context-specific and decision-related neural activity that is sufficiently matched to real-life situations.

Furthermore, presently-used cognitive tests may not be specific to the context (e.g., the sport or other activity) for which they are meant. Due to the specificity of the nervous system response to context-specific stimuli, these cognitive tests may be inadequate to properly measure cognitive skills pertinent to a given context.

SUMMARY

The problem solved concerns the neural and behavioral measurement of decisions related to presented simulations. Such measurements are employed to determine a level of cognitive skill pertinent to a given context. One example provided in this disclosure is directed to measure a response to decisions provoked by a video depicting a football scene. In such a scene, there are game performance-relevant events (e.g., a snap, or commencement of play) that are cues for a player's ensuing actions on the field. Neural and behavioral responses to these events are measured, and the resulting data is used as a profile of each individual's abilities in football-related decision making.

Although described in the context of football, the techniques disclosed herein are not unique to this sport or sporting generally. Rather, the technique of electronically marking simulated (e.g., video-based) events to be used as markers in simultaneous neuroimaging with proper post-processing may be used for various simulation-based decision settings.

Previous attempts to solve the problem of simulation-based decision-making with time-precise neural and behavioral data have created simulated scenes (e.g., sporting scenes) with computerized graphics or otherwise precisely controlled electronically-produced events (e.g., as in video game design). However, one issue is that the fidelity of these simulations is not high enough to adequately stimulate the nervous systems to evoke the context-specific and decision-related neural activity that is sufficiently matched to real-life situations.

Fidelity of a simulated event encompasses elements that contribute to how closely a recreation of the event reflects an actual event. In the example of a football scene, an audio-visual recording provides a richness of visual and audible cues that a subject (e.g., a football player) would recognize as a portrayal of such a scene. High definition recordings provide detail that can immerse the subject in the simulated environment to provoke a natural response. In this manner, a more faithful measure of the subject's cognitive skill with regard to the particular simulated event is obtained, in contrast to an animated graphic, for example.

Video provides a way to adequately simulate the visual and auditory aspects of these events and so an advantageous added element is to annotate context-relevant events within the recording. Based on an analysis of the subject's responses, neural and behavioral decision making can be judged. This approach provides an innovative solution to such a problem.

Certain existing cognitive tests are not specific to the context (e.g., the sport) for which they are meant. Due to the specificity of the nervous system response to context-specific stimuli, such cognitive tests are inadequate to effectively measure cognitive skills pertinent to a given context. Thus, the level of an expert's decision making skill could not have been satisfactorily measured.

The inventive approach of using visual, auditory, and/or tactile stimuli relevant to a given context ensures that the evoked nervous system response is specific to the context under study, hence making any cognitive assessment (via neural and/or behavioral metrics) a more complete and proper solution to the problem.

Furthermore, because the inventive techniques employ a precise time locking of context-specific decisions, a simulated event can be replayed and timed events that correspond to when a given decision was made in response to that simulated stimulus can be superimposed on the replayed recording. For the example football decision-making analysis tool, a frame within a video when a player decided that a snap had occurred can be highlighted in the video depicting a play-start (i.e., a "snap") from the line of scrimmage. A similar capability exists to measure when the player decided, for a given video, that a snap was not about to occur.

DETAILED DESCRIPTION

The systems and methods described herein are directed generally to measuring a level of expertise via neural and behavioral metrics collected in response to a particular stimulus (e.g., a cognitive event).

Data associated with "expertise" with a specific trait or skill can be collected by monitoring a nervous system reaction elicited in response to stimuli particular to that expertise. In but a few non-limiting examples, a skilled tennis player's brain responds particularly to a tennis serve; a musician's brain respond particularly to music; and a soldier's brain responds particularly to features associated with a combat environment (e.g., noise, light, vibration, etc.).

Based on experimental data, performance at an expert task is measurable when the task relevant to the expert skill is suitably simulated. One example method of simulation is an audio-visual presentation, such as a recording of a simulated tennis serve for tennis players. In other examples, the sounds of music are reproduced for musicians, whereas explosion/gunshot sounds, flashes of light, and even simulated tactile stimuli (e.g., vibrations) may be generated for training a soldier.

Accordingly, when one having a level of expert skill in recognizing and/or reacting to a particular stimulus is exposed to such a stimulus, the nervous system exhibits one or more measurable responses. The level of expert skill can be compared against an ideal measurement, against data compiled through trial, or against the expert's own historical data. Thus, expertise can be associated with a level of cognitive skill pertinent to a given context. This level of skill can be assigned a score used as a tool for ready comparison between different subjects presented with a common stimulus.

Each stimulus can be presented virtually, or reproduced in a recorded form. Thus, the tennis serve was not the actual visual stimulus the player sees at on the court. Just like the recording of a piece of music, and its playback on speakers/headphones, is not really what it's like to hear the actual auditory stimulus. By using video (e.g., HD video, virtual reality immersion, or 360 video), instead of animation, for tennis, the simulations are much more effective at eliciting the neural markers of expertise. In some scenarios, basic visual features associated with the activity may be animated. However, in some activities a representative animation is not possible (e.g., soccer), video is to be relied upon. Thus, in order to measure neural expertise and provide that analysis back to the user, the video is integrated with the neural and behavioral response measurements. This is a beneficial way to measure a response to visual (and potentially auditory and tactile) recognition.

A direct comparison of responses to low fidelity recordings (e.g., animated and/or reconstructed video and/or audio) versus high fidelity recordings (e.g., recordings exclusive of animation, such as live-action recordings) reveals a different engagement of neural structures when exposed to recordings of different fidelity. In particular, a neural response associated with the perception and interpretation of agency is greater when identical physical movements were performed by real rather than animated agents.

In other words, the blood flow in areas associated with perception, in the present example the perception of other people's movements, is greater for real (high fidelity) movements verses animated (high fidelity) movements. Thus, being presented with live-action video movement has a different impact (e.g. by activating different neural substrates) on brain response than animation of the exact same movements.

The greater neural response to the high fidelity video therefore provides a more complete, faithful set of data by which to judge an expert's analysis of a cognitive event. Presentation of high fidelity recordings elicits different, stronger cognitive recognition over presentation of artificially created animation, much less static images.

Figure 1:
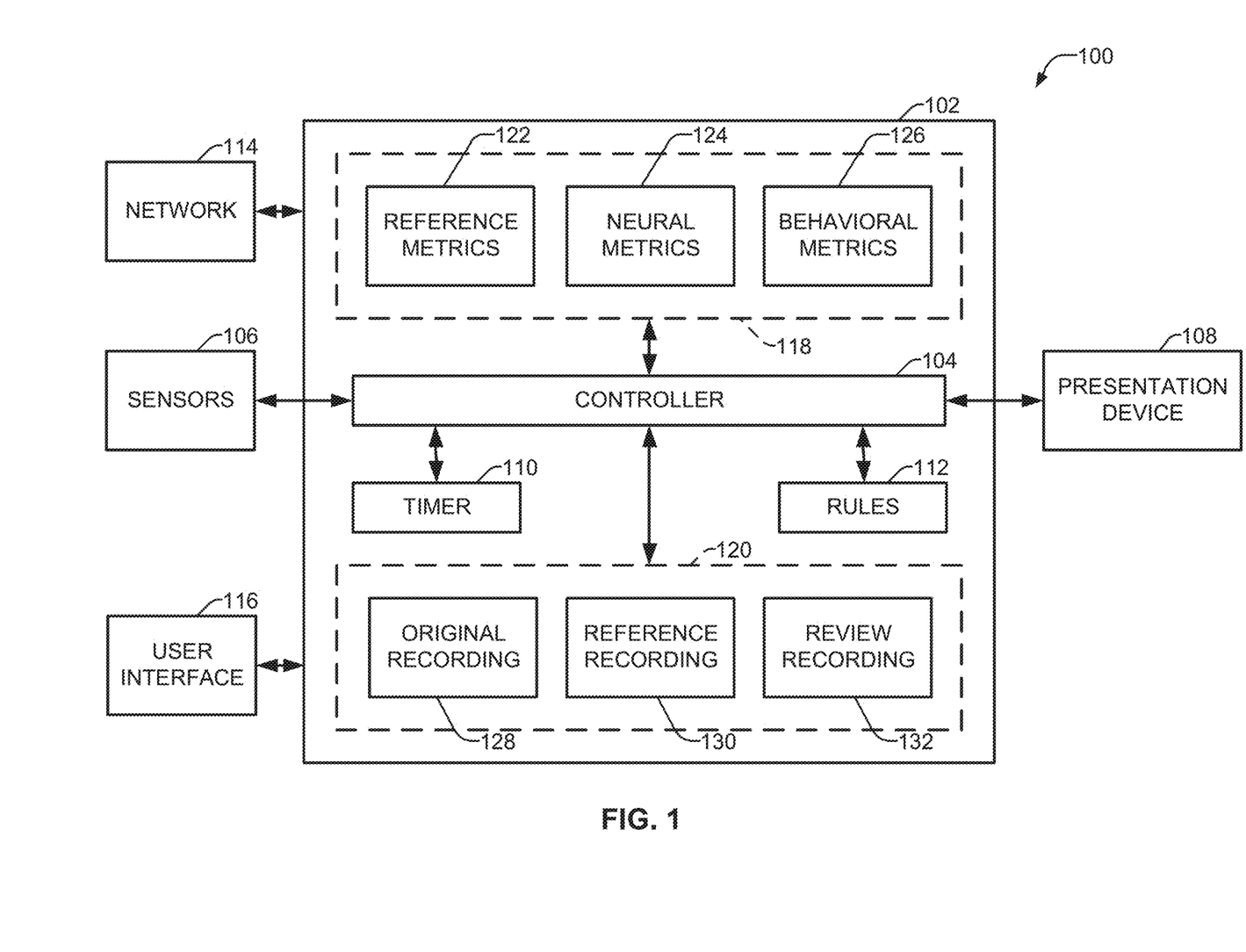
FIG. 1 shows an example block diagram of a system to perform the simulation-based decision analysis in accordance with aspects of this disclosure.

FIG. 1 illustrates an example system that may be employed to perform the processes described herein. The system 100 includes a controller 104 housed in a processor 102, the controller to execute machine readable instructions that cause various software and hardware to interact. In the example of FIG. 1, the controller 104 is connected to one or more sensors 106 to monitor, collect, and/or transmit data from a subject. Sensors 106 can include an electroencephalogram ("EEG") or other neural activity monitor, as well as behavioral sensors, such as a user interface (e.g., mechanical or electrical) and/or a passive sensor (e.g., cameras). Multiple sensors, of a like or different kind, can be used simultaneously, at various times throughout the monitoring period, in combination and/or independently.

The controller 104 is connected to a presentation device 108. Presentation device 108 may represent various presentation media that may be employed to evoke a realistic response in a subject. For example, a high definition audio-visual display is designed to immerse the subject in a high fidelity simulated environment. The audio-visual display can be a virtual reality ("VR") apparatus, as well as a device that provides a 360 degree view of the displayed content. Additionally or alternatively, presentation device 108 can be configured to replicate other sensory cues, such as vibrations, temperature, changes in pressure, etc. Based on the desired environment, a combination of presentation devices 108 may be employed to provide a faithful simulation of a stimulation event, or a specific presentation device 108 can be employed independently, depending on the particular stimulus presented to the subject.

A timer 110 is connected to controller 104, and can be within processor 102, may be located externally, or may be within the controller 104 itself. Timer 110 is employed to mark precise temporal identifiers of consequence associated with a stimulus event. For example, a stimulus event is a cognitive event that can be objectively identified and assigned one or more metrics (e.g. timing, Go/No Go, Cognitive Load) in accordance with one or more rules. In another example, a recording is created with one or more precise time markings embedded therein.

One or more rules 112 are connected to controller 104. Rules 112 that are associated with a particular stimulus event (e.g., cognitive event) are governed by a specific set of rules associated with the environment in which the stimulus is operating (e.g., an action in a particular sporting event, i.e. football). When applied to a recording, the rules 112 may identify the stimulus event and other features of the recording that are useful in analysis of the context-specific decision making process of the subject. In an example, rules 112 can be a library of rules stored within a computer readable media within processor 102, or may be introduced through a network 114 or a user interface 116. Moreover, an administrator may input specific rules to correspond to a specific stimulus event. The rules 112 may be applied to the recording automatically, or may be applied and/or modified by the administrator.

The controller 104 is connected to a metrics storage media 118 and a recording storage media 120, such as a machine readable medium (e.g., solid-state media, optical storage device, a networked or "cloud" storage medium, etc.). Media 118 and 120 dynamically store data as metrics are compiled and as recordings are updated and/or created, respectively. For example, each rule 112 or set of rules relevant to the specific event and/or environment can be quantified by one or more metrics. The metrics are intended to both identify a particular component of the stimulus event to measure a particular objective characteristic of the event (e.g., a timing component defining a particular feature associated with the stimulus event), as well as a comparatively subjective metric (e.g., a quality assessment regarding strength, conviction or understanding of a subject's understanding of the stimulus event) corresponding to a measured neurological response from the subject while the subject interacts with a recording of the event.

Metrics are compiled throughout the evaluation process. In an example, reference metrics 122 are assigned to original recording 128. Original recording 128 can come in a variety of forms. For example, original recording 128 can be an audio-visual presentation, audio only, a virtual reality presentation such as a 360 viewing display, and other forms of audio-visual presentation suitable for simulating a real-life event. Further, original recording 128 can form an immersive environmental system, such as a training room. In such an environment, additional and alternative stimuli can be introduced, such as temperature, pressure, olfactory stimuli, vibration, and movement, among many others, by employing suitable devices and/or systems to generate a corresponding output. Presenting the recording in an immersive environment can aid in evoking a real-world response from a subject.

Reference metrics 122 serve as an objective standard against which other metrics compiled during analysis of a subject are compared, such as timing associated with a stimulus event. In other words, after application of a set of rules 112, reference metrics 122 are identified to set a benchmark upon with other metrics are compared.

Upon application of the rules 112 and generation of reference metrics 122, a reference recording 130 is created to incorporate data associated with the reference metrics 122. The data corresponding to reference metrics 122 can include timing data, comparative data, modified recording elements, etc., to provide a comparative tool during subject testing.

As a further example, each high fidelity recording contains a plurality of elements. These elements can include video or audio elements associated with a recording, such as color, volume, focus, etc. These elements are intended to be recognizable to one presented with the recording element. Thus, modification of one or more of the recording elements may alert a subject to a feature associated with a stimulus event to correspond to reference metrics 122.

During presentation, neural responses of a subject are collected. Neural metrics 124 represent data collected from the subject by sensor 106 (e.g., an EEG, or other suitable device) simultaneously with a presentation of the high fidelity recording. Also during presentation, behavioral metrics 126 are collected from the subject through a variety of methods and/or devices simultaneously with the presentation of the high fidelity recording. Collection methods and/or devices for behavioral metrics 126 include graphical interfaces in communication with a processing unit, a mechanical tool capable of recording at least time and an instance of a response, as well as passive observation from a sensor (e.g., one or more cameras), to name but a few possible examples.

In the example where the high fidelity recording is an audio/visual presentation, the review recording 132 may include audio and/or visual identifiers (e.g., text) of each metric (e.g. reference metrics 122, neural metrics 124, behavioral metrics 126, etc.), as well as modified recording elements. For instance, review recording 132 is a compilation of each relevant metric and data. Thus, an audio/visual review recording can include, for example, an overlay containing one or more metrics such that a subject can view and compare relative aspects of neural metrics 124 and behavioral metrics 126 with respect to a corresponding reference metric 122.

Furthermore, the modified recording elements can alert the subject to items of consequence associated with the stimulus event. For instance, a color video presentation can fade to grey scales at the time of the stimulus event corresponding to a reference metric 122. Elements of a presentation can also include other visual cues (e.g., flashing, highlighting elements such as a figure on the screen, etc.), audio cues (e.g., an alarm sound, a silencing of the audio playback, isolation of a particular sound, etc.), as well as tactile or haptic feedback (e.g., from a wearable device) when the presentation system 108 so provides.

Figure 2:
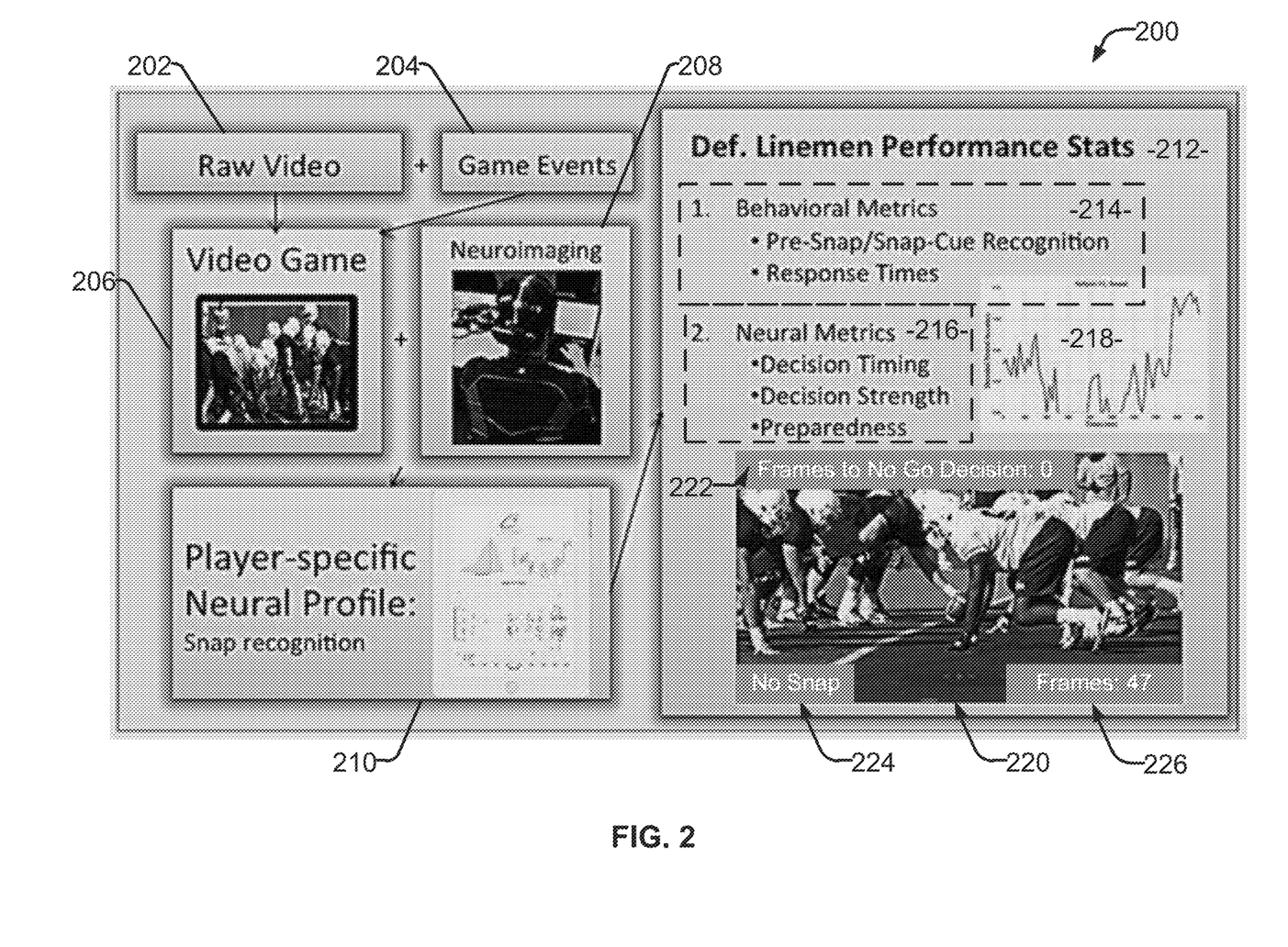
FIG. 2 shows an example overview of a process by which simulation-based decision making can be assessed, in accordance with aspects of this disclosure.

FIG. 2 shows an example overview of a process 200 by which simulation-based (e.g., video-based) decision making assessment may be performed in a particular context of football, specifically a stimulus event represented as a "snap" for defensive linemen using the example system of FIG. 1. Starting in the upper left corner, an unmodified recording (e.g., "Raw Video" 202) is annotated with one or more metrics in accordance with one or more rules to define the stimulus event (e.g., "Game Events" 204), combining both to create a reference recording (e.g., "Video Game" 206) in which a subject must decide if a given simulation shows or does not show a snap. If the subject recognizes a snap as shown in the presented recording, then the subject must decide to hit a specific button on a computer, tablet, other computerized interface, mechanical switch, or some alternative indicator of a behavioral response. Simultaneously, "Neuroimaging" 208 is done on the subject, shown in the second row on the left side of the Figure. The output of the "Video Game" 206+"Neuroimaging" 208 is a "Player-specific Neural (and Behavioral) Profile," 210 in this example for "Snap recognition".

The output of example metrics, or "Performance Stats" 212, available for a defensive lineman, as illustrated in this example, is shown on the right side of FIG. 2. Metrics comprise two categories: "Behavioral Metrics" 214 and "Neural Metrics" 216. For this particular example, behavioral metrics 214 represent accuracy of the defensive lineman's "Pre-Snap/Snap-Cue Recognition" and physical "Response Times" in doing so. Neural metrics 216 for this example—and other simulation-based recordings presenting cognitive events—are "Decision Timing" and "Decision Strength." As in this example, for decision-events that are cued by a prior event, neural metrics 216 may comprise of a "Preparedness" measurement gleaned also from neuroimaging data. In this manner, the neural data leading up to (as well as following) the simulated event is used to generate another measure of the subject's cognitive skill. The inset FIG. 218 to the right of neural metrics 216 shows a time course of algorithmic decoding of neuroimaging data, where a greater height of the line indicates a subject's ability to measure decision-related activity, such as "Go" or "No-Go" decisions, in response to a viewed snap. The first time point is the commencement of the presentation (e.g., the video is displayed to the subject). As most snaps occur towards the end of this and other snap videos, the rise in the line towards the end of the time course is representative of an increased recognition of a snap event in the recording. Thus, the preparedness of a subject can correspond to a measure of the neural and behavioral metrics leading up to the moment of decision.

Finally, the figure below shows a frame 220 for when a decision was made that a snap had not occurred. This frame 220 can be highlighted (e.g., shown in black-and-white), while all other frames of the video are in the original form (e.g., color) used in the recording as originally presented to the subject. Upon playback, this modified recording is how the decision event is projected back into the context-relevant space, which in this case is the original video, though it need not be in other examples. In this example, within from 220 is displayed information regarding reference metrics. For instance, "Frames to Go" 222, "No Snap" 224, and "Frame: 47" 226, are identified as reference metrics to the viewer. This is another novelty of such the approach described herein.

Figure 3:
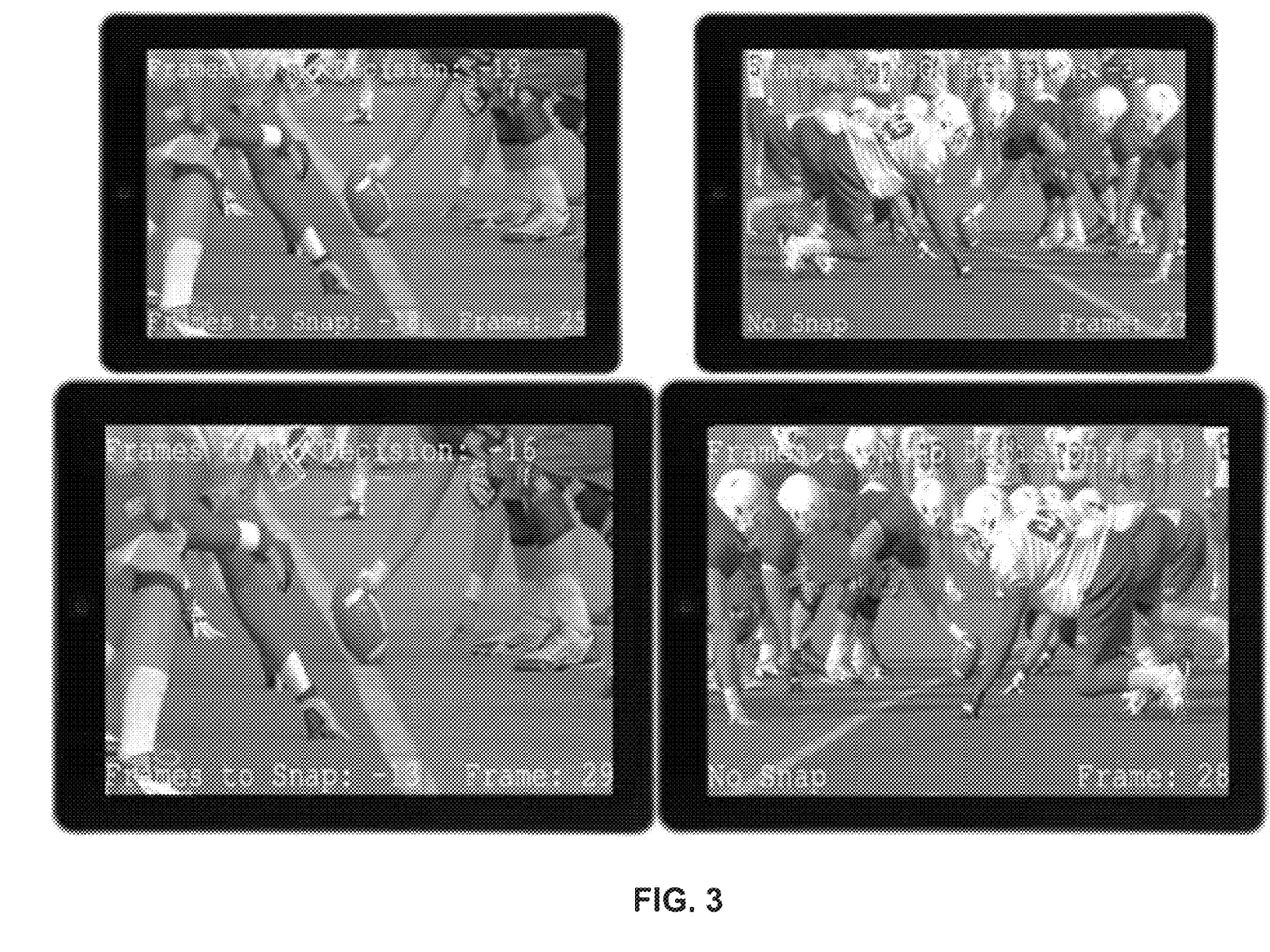
FIG. 3 shows example screen shots from videos for which simulation-based decision making can be assessed, in accordance with aspects of this disclosure.

FIG. 3 shows four screen shots from videos for which decisions (e.g., metrics) have been projected back into the original recording. In the present example, the metrics associated with the stimulus event have been included in the video frames associated with the event stimulus as text as an overlay. The two left frames illustrate a subject's recognition of "Go" (i.e., "snap") decisions, while the two right frames illustrate recognition of "No-Go" (i.e., "non-snap") decisions. On each frame of the video, text is added to show how many frames until the context-relevant event (e.g., "Frames to Snap" in bottom left corner or "No Snap", if no such event occurs in the given video). In the top left corner of each video, text is also added to show how many frames until the given decision occurs (e.g., "Frames to Go Decision" or "Frames to No-Go Decision"). All videos may also show in the upper right corner what frame number, for reference. In this manner, a given subject's decisions for a given video are mapped back into the original stimulus space.

In the example of FIG. 3, text has been added to the video as an indicator of the time-precise nature of the stimulus events as well as the decision metrics in response to such an event. Additional and/or alternative identifiers are also considered. In some examples, the color and or intensity of the video can change as the video progresses toward a time associated with a stimulus event. An audible alert can also be provided, such as a verbal explanation of the metric, or a gradual change in a portion of the audible signal to climax at a specific point of interest associated with the stimulus event. In an example presenting a fully immersive experience, the identifiers may be associated with elements other than audio and visual cues. In some examples, the subject can be connected to a mechanical device that provides physical feedback associated with the stimulus event, such as a vibrating wearable device. In other examples, environmental conditions can be recreated to provide a more faithful experience, such as changes in temperature, pressure, the sensation of wetness, wind, or a sense of movement (e.g., a g-force), to name but a few.

In the example of FIG. 3, only neural decision events have been superimposed on the original stimulus space, but any neural and/or behavioral event may be projected back into this original stimulus space, given that the precision in recording its timing is sufficient and the presentation system so provides.

Figure 5:
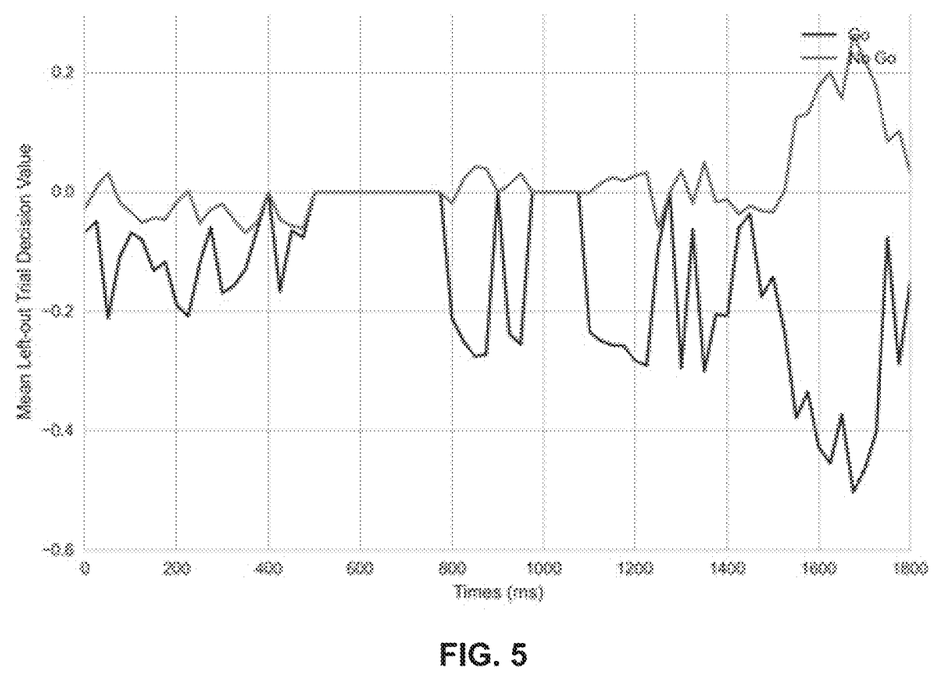
FIG. 5 shows example data of decision timing as a function of time, in accordance with aspects of this disclosure.
Figure 6:
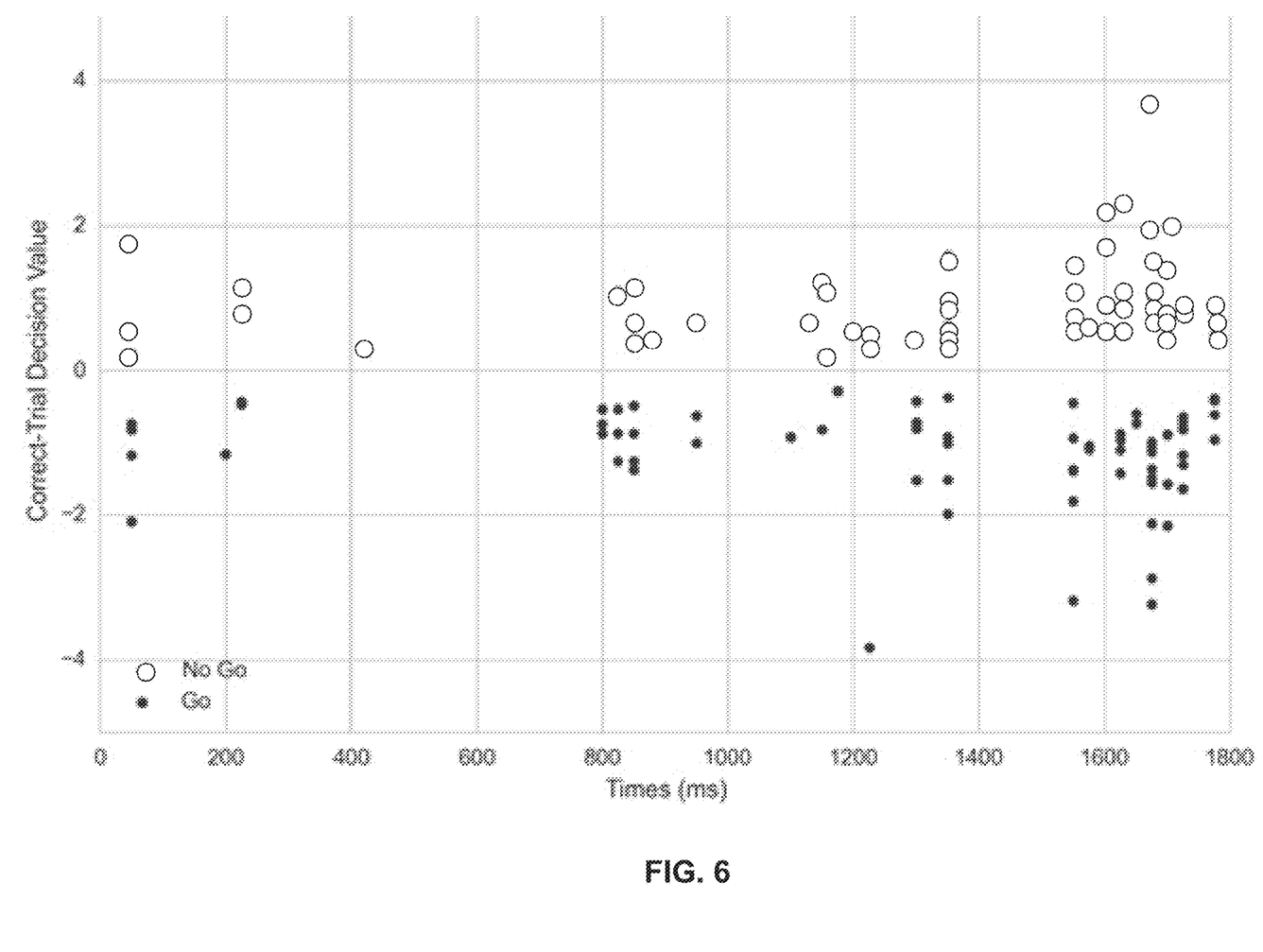
FIG. 6 shows example data for a context-specific event, in accordance with aspects of this disclosure.

Example results achieved by the inventive techniques described herein include the provision of a context-specific representation of neural and behavioral responses to simulation-based stimuli, illustrated herein by the example in the football context. For instance, the results shown in FIGS. 4 to 6 provide experimental data which represents metrics to be superimposed onto original videos to show for each subject when he/she decided a situation-relevant event had occurred based on the video stimulus.

The experimental results achieved by the inventive techniques described herein provide the ability to measure the timing of neural and behavioral responses evoked by a video. The example of FIG. 4 shows the time course of algorithmic ability to decode decisions evoked in response to a video presenting a stimulus event. The video begins at 0 ms on the x-axis and continues until the end of the video, approximately 1800 ms. The y-axis represents the "Decoded Neural Accuracy," which is a measurement based on a metric called the Receiver Operator Characteristic (ROC) that quantifies the ability of a computer algorithm to properly classify data, which in this case is neuroimaging data. The curve is thus the time-resolved accuracy in decoding neural activity, which in this case is for two types of decisions (in this example, decisions that there was a snap and decisions that there was not, e.g., Go/No Go).

Figure 4:
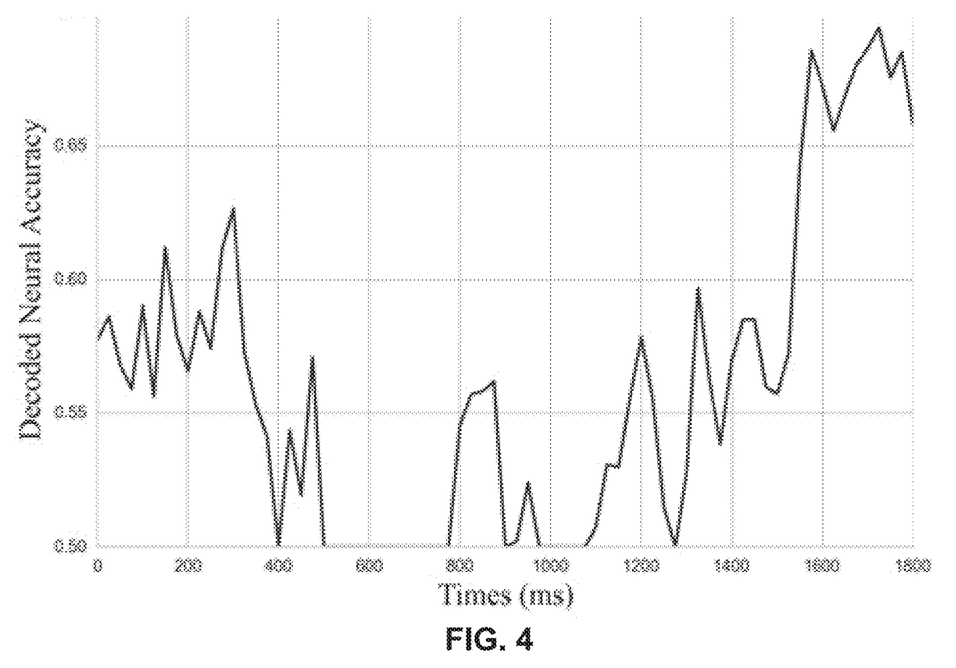
FIG. 4 shows example data of a decoded neural measurement, in accordance with aspects of this disclosure.

Using the results shown in FIG. 4, decision strength for a given decision at each point in the trial may be measured. This information is then deliverable via the Profile described in FIG. 2 as "Decision Strength." FIG. 4 shows this for "Go" and "No Go" decisions in the example of the video-based decision-making analysis for the football context. It is noted that even as the subject may decide that the snap is a "Go", and the data confirms that the subject made this decision with a high level of self-assurance, that decision may be incorrect according to the rules. In other words, strength of a decision does not correlate to correctness of that decision. Similarly, relative weakness of a decision does not necessarily correlate to an incorrect decision.

Using the peak decision strength in each video-viewing, the decision that occurs in each video-viewing directly from the neuroimaging data can be measured. This can be plotted for any given decision, as shown in FIG. 6 for "Go" (solid circle) and "No Go" (open circle) decisions in the example of a football-context video-based decision-making assessment system.

There are several fundamental differences between the inventive techniques solution and prior ones. First, looking at the stimulation of the nervous system (i.e., the "video game"), videos are used by the inventive techniques to make a game that may be crafted to stimulate the nervous system in a way to effectively measure decisions in the given context (e.g., in this example, football). Then, having measured these decisions in time on both a neural and behavioral level, the timing of these decisions may be projected back into the stimulus space (e.g., the black-and-white highlighted frame shown in FIG. 2). Second, considering that previous video-based decisions have not undergone such analysis, the addition of a neuroimaging system is a difference between the inventive techniques and prior techniques.

At least one functional difference between the techniques disclosed herein and certain prior ones is that when decisions are made can be measured relative to video-based stimulation of the nervous system. Because of the timing of relevant events in a given simulation-based context representation, inventive techniques measure decision-timing and evolution in relation to specified events.

Figure 7:
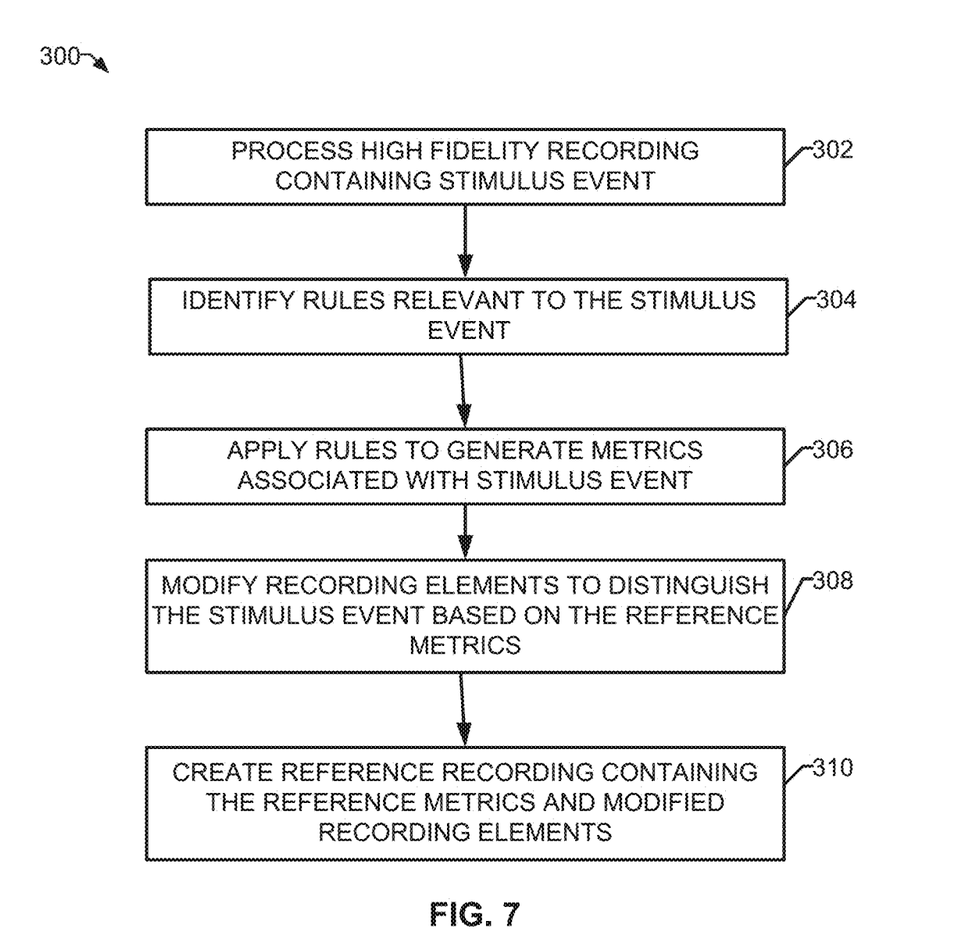
FIG. 7 is a flowchart illustrating an example method which may be executed by the system of FIG. 1, in accordance with aspects of this disclosure.
Figure 8:
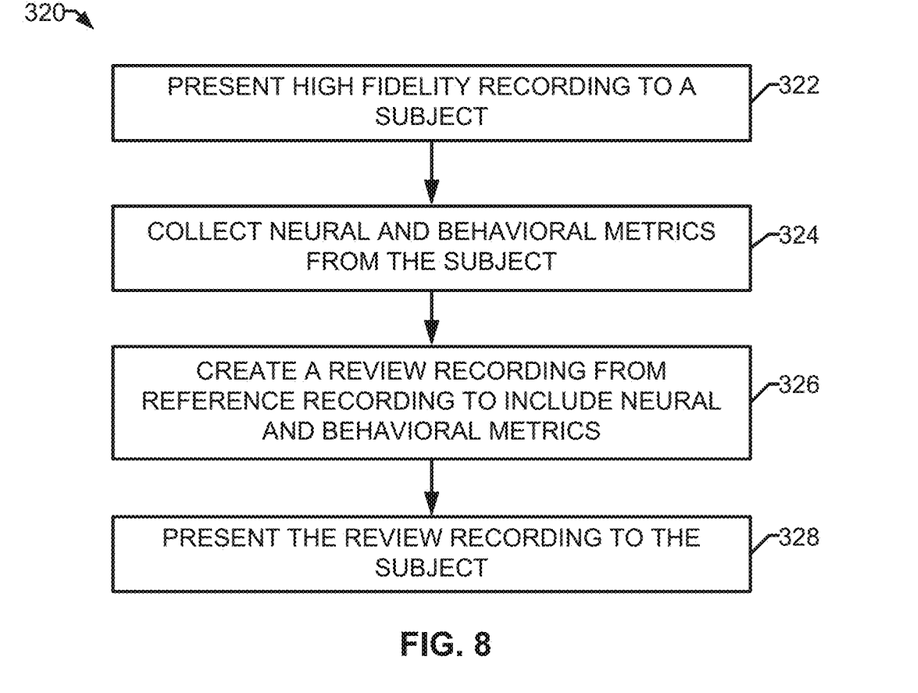
FIG. 8 is another flowchart illustrating an example method which may be executed by the system of FIG. 1, in accordance with aspects of this disclosure.

FIGS. 7 and 8 are flow charts of example methods for generating a review recording. FIG. 7 illustrates an example method 300 of creating a reference recording, such as the reference recording 130 of FIG. 1. At block 302, a high-fidelity recording containing a stimulus event is processed (e.g., captured in a recording, acquired in presentable format from a content originator, created in a suitable environment, etc.). The processing can include identifying a timing component associated with the stimulus event, and changing, adding, and/or removing recording elements in the high-fidelity recording. This can be done for a given time period before and/or after the stimulus event. At block 304, rules relevant to the stimulus event are identified. At block 306, the rules are applied to generate metrics associated with stimulus event. At block 308, the recording elements are modified to distinguish the stimulus event based on the reference metrics. At block 310, a reference recording containing the reference metrics and modified recording elements is created.

FIG. 8 illustrates an example method 320 of creating a review recording, such as the review recording 132 of FIG. 1. Referring to FIG. 8, at block 322, the high-fidelity recording, such as original recording 128, is presented to a subject. At block 324, neural and behavioral metrics are collected from the subject, such as by the sensor 106. At block 326, a review recording (e.g., review recording 132) is created from the reference recording (e.g., reference recording 130) to include neural and behavioral metrics (e.g., neural metrics 124, behavioral metrics 126). At block 328, the review recording is presented to the subject, such as by presentation device 108.

The present invention has been described in the terms of the preferred example and it is recognized that equivalents, alternatives, and modifications, aside from those expressly stated, are possible and within the scope of the disclosure.

The present methods and systems may be realized in hardware, software, and/or a combination of hardware and software. The present methods and/or systems may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may include a general-purpose computing system comprising a processor with a program or other code that, when being loaded and executed, controls the computing system such that it carries out the methods described herein. Another typical implementation may comprise one or more application specific integrated circuit or chip. Some implementations may comprise a non-transitory machine-readable (e.g., computer readable) medium (e.g., FLASH memory, optical disk, magnetic storage disk, or the like) having stored thereon one or more lines of code executable by a machine, thereby causing the machine to perform processes as described herein. As used herein, the term "non-transitory machine-readable medium" is defined to include all types of machine readable storage media and to exclude propagating signals.

As utilized herein the terms "circuits" and "circuitry" refer to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. In other words, "x and/or y" means "one or both of x and y". As another example, "x, y, and/or z" means any element of the seven-element set $\{(x), (y), (z), (x, y), (x, z), (y, z), (x, y, z)\}$. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. For example, block and/or components of disclosed examples may be combined, divided, re-arranged, and/or otherwise modified. Therefore, the present methods and/or systems are not limited to the particular implementations disclosed, but include all implementations falling within the scope of the appended claims, both literally and under the doctrine of equivalents.

What is claimed is:

1. A method to analyze decision-making, the method comprising:

accessing, by a processor, at least one storage medium that includes a recording comprising a stimulus event and one or more rules associated with the stimulus event;

presenting the recording by a presentation device;

receiving one or more neural metrics from at least one neural sensor in response to the presentation, wherein the one or more neural metrics correspond to a measured neurological response to the stimulus event;

applying the one or more rules to the recording to generate one or more reference metrics associated with the stimulus event;

modifying one or more elements of the recording based on the one or more reference metrics to distinguish the stimulus event within the recording;

adding the one or more neural metrics to the recording; and presenting a review recording comprising the one or more neural metrics and the modified recording by a presentation device.

2. The method as defined in claim 1 further comprising:
receiving one or more behavioral metrics from at least one other sensor in response to the presentation, wherein the one or more behavioral metrics correspond to a measured physical response to the stimulus event; and
presenting the review recording comprising the one or more reference metrics, the one or more neural metrics and the one or more behavioral metrics by a presentation device.

3. The method as defined in claim 1 further comprising generating at least one time marker for each of the one or more reference metrics based on a timer, the one or more neural metrics and the one or more behavioral metrics in response to the application of the one or more rules to the high-fidelity recording.

4. The method as defined in claim 3 further comprising processing the review recording to modify the one or more recording elements to correspond with a time marker associated with the one or more reference metrics.

5. The method as defined in claim 3 further comprising processing the review recording to modify the one or more recording elements to correspond with at least one time marker associated with the one or more neural metrics and the one or more behavioral metrics.

6. The method as defined in claim 1, wherein the one or more recording elements corresponds to an output in a form perceptible to a subject.

7. The method as defined in claim 6, wherein the one or more recording elements include at least one of a visual, an audio, or a tactile response.

8. The method as defined in claim wherein presenting the review recording further comprises:
generating one or more identifiers based on the one or more review metrics, the one or more neural metrics, and the one or more behavioral metrics, wherein the identifier is one of a text, a visual or an auditory identifier;
overlaying the one or more identifies onto the review recording; and
presenting the review recording and the one or more identifiers simultaneously to a subject.

9. The method as defined in claim 2, wherein a user input is collected by the at least one neural sensor or the at least one other sensor and transmitted to the controller by one of a wired or a wireless communication.

10. The method as defined in claim 9, wherein the at least one neural sensor or the at least one other sensor comprises at least one of an electroencephalogram, a mechanical switch, and a camera.

11. The method as defined in claim 1, wherein the recording comprises a live-action audio-visual presentation.

12. The method as defined in claim 1, wherein the recording comprises an immersive training environment, wherein the recording elements comprise at least two of a temperature, a pressure, an olfactory stimulus, vibration, and movement.

13. At least one non-transitory, machine-readable storage device comprising machine readable instructions which, when executed, cause at least one processor to:
process a recording comprising a stimulus event;
present the recording by a presentation device;
receive one or more neural metrics from at least one sensor in response to the presentation, wherein the one or more neural metrics corresponding to a measured neurological response to the stimulus event;
identify one or more rules to define one or more metrics associated with the stimulus event;
apply the one or more rules to the recording to generate one or more reference metrics associated with the stimulus event;
modify one or more recording elements of the recording based on the one or more reference metrics to distinguish the stimulus event within the recording;
add the one or more neural metrics to the recording; and
present a review recording comprising the one or more neural metrics and the modified recording by the presentation device.

14. The at least one non-transitory, machine-readable storage device comprising machine readable instructions as defined in claim 13, wherein the instructions, when executed, cause the processor to:
present the recording by one or more of a visual display, an audible transmission, and a tactile response device;
receive one or more behavioral metrics from at least one user input in response to the presentation, wherein the one or more behavioral metrics corresponding to a measured physical response to the stimulus event; and
create the review recording comprising the one or more reference metrics, the one or more neural metrics and the one or more behavioral metrics.

15. The at least one non-transitory, machine-readable storage device comprising machine readable instructions as defined in claim 13, wherein the instructions, when executed, cause the processor to present the review recording to a subject.

16. The at least one non-transitory, machine-readable storage device comprising machine readable instructions as defined in claim 13, wherein the instructions, when executed, cause the processor to:
compare a timing component of the one or more reference metrics to a timing component of the one or more neural metrics and/or the one or more behavioral metrics; and
generate a score corresponding to a level of expertise based on the comparison.

17. The at least one non-transitory, machine-readable storage device comprising machine readable instructions as defined in claim 13, wherein the instructions, when executed, cause the processor to:
analyze the one or more neural metrics; and
classify each of the one or more neural metrics as corresponding to at least one of a decision value and a preparedness value.

18. The at least one non-transitory, machine-readable storage device comprising machine readable instructions as defined in claim 17, wherein the instructions, when executed, cause the processor to:
compare the decision value to an optimized decision value based on the reference metrics; and
generate a decision value score based on the comparison.

19. The at least one non-transitory, machine-readable storage device comprising machine readable instructions as defined in claim 18, wherein the instructions, when executed, cause the processor to:
compare the preparedness value to an optimized preparedness value based on the reference metrics; and
generate a preparedness value score based on the comparison.

20. A method to analyze decision-making, the method comprising:

processing, by a processor, a live-action recording comprising a stimulus event;
identifying one or more rules to define one or more metrics associated with the stimulus event;
applying the one or more rules to the live-action recording to generate one or more reference metrics associated with the stimulus event;
modifying one or more recording elements of the live-action recording based on the one or more reference metrics to distinguish the stimulus event within the live-action recording;
creating a reference recording comprising the live-action recording;
presenting, by a presentation device, the live-action recording by one or more of a visual display, an audio speaker, and a tactile response device;
receiving one or more neural metrics and one or more behavioral metrics from at least one user input in response to the presentation, wherein the one or more neural metrics correspond to a measured neurological response to the stimulus event and the one or more behavioral metrics correspond to a measured physical response to the stimulus event;
creating a review recording comprising the reference recording, the one or more neural metrics and the one or more behavioral metrics;
presenting, by the presentation device, the review recording;
comparing a timing component of the one or more reference metrics to a timing component of the one or more neural metrics and/or the one or more behavioral metrics; and
generating a score corresponding to a level of expertise based on the comparison.

* * * * *